US012268526B2

(12) United States Patent
Chung et al.

(10) Patent No.: US 12,268,526 B2
(45) Date of Patent: Apr. 8, 2025

(54) TRANSPARENT DEVICE WITH BIO-SIGNAL ACQUISITION AND FEEDBACK CAPABILITIES

(71) Applicant: HAOSEN TECH CO., LTD., New Taipei (TW)

(72) Inventors: Kuo-Yuan Chung, New Taipei (TW); Ruei-Ren Luo, Taipei (TW)

(73) Assignee: HAOSEN TECH CO., LTD., New Taipei (TW)

( * ) Notice: Subject to any disclaimer, the term of this patent is extended or adjusted under 35 U.S.C. 154(b) by 329 days.

(21) Appl. No.: 17/886,037

(22) Filed: Aug. 11, 2022

(65) Prior Publication Data

US 2023/0057204 A1 Feb. 23, 2023

(30) Foreign Application Priority Data

Aug. 20, 2021 (TW) .................................. 110130774

(51) Int. Cl.
*A61B 5/00* (2006.01)
*A61B 5/0205* (2006.01)
*A61B 5/26* (2021.01)
*A61B 5/282* (2021.01)
*A61B 5/024* (2006.01)

(52) U.S. Cl.
CPC .......... *A61B 5/6887* (2013.01); *A61B 5/0006* (2013.01); *A61B 5/0008* (2013.01); *A61B 5/0017* (2013.01); *A61B 5/02055* (2013.01); *A61B 5/26* (2021.01); *A61B 5/282* (2021.01); *A61B 5/7415* (2013.01); *A61B 5/742* (2013.01);

(Continued)

(58) Field of Classification Search
None
See application file for complete search history.

(56) References Cited

U.S. PATENT DOCUMENTS

| 2002/0174578 A1* | 11/2002 | Ross | G09F 19/02 40/409 |
| 2006/0009698 A1* | 1/2006 | Banet | A61B 5/26 128/903 |

(Continued)

FOREIGN PATENT DOCUMENTS

| CN | 104755020 A | 7/2015 |
| TW | 201627813 A | 8/2016 |

(Continued)

*Primary Examiner* — Catherine M Voorhees
*Assistant Examiner* — James Moss
(74) *Attorney, Agent, or Firm* — Li & Cai Intellectual Property (USA) Office (57) ABSTRACT

A transparent device with bio-signal acquisition and feedback capabilities is provided, and includes a base that includes at least one actuator, a transparent container connected to the base, first and second electrodes disposed on the base, a body temperature sensor, a photoplethysmography (PPG) sensor module, and a bio-signal acquisition module that has an electrocardiographic (ECG or EKG) sensor function and acquires an ECG signal, a PPG signal, and a body temperature signal of the user. The bio-signal acquisition module determines physiological indices by using a preset algorithm and controls the at least one actuator to provide corresponding visual or auditory feedbacks in real time according to the physiological indices and an extended cardiac index of the user.

7 Claims, 4 Drawing Sheets

(52) U.S. Cl.
CPC ... *A61B 5/02427* (2013.01); *A61B 2560/0214* (2013.01); *A61B 2562/0271* (2013.01)

(56) References Cited

U.S. PATENT DOCUMENTS

| | | | | |
|---|---|---|---|---|
| 2010/0173561 | A1* | 7/2010 | Tseng | H04N 5/64 |
| | | | | 348/739 |
| 2012/0088985 | A1* | 4/2012 | Schiavenato | G16H 40/63 |
| | | | | 600/301 |
| 2013/0310659 | A1* | 11/2013 | Kawachi | A61B 5/02125 |
| | | | | 600/301 |
| 2015/0288914 | A1* | 10/2015 | Minneman | G09F 19/12 |
| | | | | 348/552 |
| 2020/0305739 | A1* | 10/2020 | Getman | A61B 5/1455 |

FOREIGN PATENT DOCUMENTS

| | | |
|---|---|---|
| TW | M586596 U | 11/2019 |
| TW | M622469 U | 1/2022 |

\* cited by examiner

TRANSPARENT DEVICE WITH BIO-SIGNAL ACQUISITION AND FEEDBACK CAPABILITIES

CROSS-REFERENCE TO RELATED PATENT APPLICATION

This application claims the benefit of priority to Taiwan Patent Application No. 110130774, filed on Aug. 20, 2021. The entire content of the above identified application is incorporated herein by reference.

Some references, which may include patents, patent applications and various publications, can be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a device that has a transparent container, and more particularly to a transparent device that has bio-signal acquisition and real-time feedback capabilities.

BACKGROUND OF THE DISCLOSURE

In recent years, with the increasing emphasis on health, people are wearing various devices, such as wristwatches and wristbands, to measure and collect daily bio-signals as a main interface for daily tracking and managing of mental and physical stress, thus gradually achieving effects of health management by accumulating a large amount of data over a long period of time and adopting corresponding changes in lifestyle. However, people leading busy lifestyles are often unable to repeatedly perform the repetitive and uninteresting measurement actions for an extended period of time, and thus cannot effectively achieve benefits of health management. Therefore, a feedback can be provided, as appropriate, through decorative objects in daily life to offer encouragement for people to continue measuring their bio-signals and thereby relieving stress.

SUMMARY OF THE DISCLOSURE

In response to the above-referenced technical inadequacy, the present disclosure provides a transparent device that has bio-signal acquisition capability, and is capable of providing a feedback in real time for bio-signals that are acquired.

In one aspect, the present disclosure provides a transparent device with bio-signal acquisition and feedback capabilities. The transparent device includes a base, a transparent container, a first electrode, a second electrode, a body temperature sensor, a photoplethysmography (PPG) sensor module, and a bio-signal acquisition module. The base includes at least one actuator. The transparent container is connected to the base, and the at least one actuator extends into the transparent container. The first electrode is disposed on the base. The second electrode is disposed on the base. The body temperature sensor is disposed on the base. The photoplethysmography (PPG) sensor module is disposed on the base. The bio-signal acquisition module has an electrocardiographic (ECG or EKG) sensor function. The bio-signal acquisition module is electrically connected to the first electrode and the second electrode, and is in contact with two hands of a user at a same time through the first electrode and the second electrode, so that the bio-signal acquisition module acquires an ECG signal of the user; or the bio-signal acquisition module is in contact with the hands of the user through the PPG sensor module, so as to acquire a PPG signal of the user is acquired; or the bio-signal acquisition module is in contact with the hands of the user through the body temperature sensor, so as to acquire a body temperature signal of the user; further, the bio-signal acquisition module determines physiological indices of the user by using a preset algorithm, and controls the at least one actuator to provide corresponding visual or auditory feedbacks in real time according to the physiological indices and an extended cardiac index of the user.

In certain embodiments, the physiological indices that are fed back to the user in real time, or are recorded, are at least one of a body temperature, a heart rate (beats per minute, BPM), a heart rate variability (HRV), a peripheral oxygen saturation (SpO2), a heart age, a blood pressure estimate, and a risk alert for excessive heart rate. The extended cardiac index that is fed back to the user in real time is a psychological or physiological index determined by using a preset algorithm according to physiological data, ECG data, and PPG data of the user, and is at least one of a mood index, a stress index, a caffeine intake index, and a heart risk index.

In certain embodiments, the at least one actuator has a color lamp that is electrically connected to the bio-signal acquisition module, so as to provide a feedback of the physiological state of the user in real time through the color lamp being switched on and switched off, and a change of light color. The at least one actuator has an audio player that is electrically connected to the bio-signal acquisition module, so as to provide a feedback of the physiological state of the user in real time through an activation of music and a change of volume of the audio player. The at least one actuator has a temperature controller that is electrically connected to the bio-signal acquisition module, and at least one color-changeable decorative model that senses changes in temperature is disposed in the transparent container, and is electrically connected to the temperature controller so that the at least one color-changeable decorative model produces corresponding visual changes through temperature control generated by the temperature controller and provides a feedback of the physiological state of the user in real time. The at least one actuator has a rotation motor disposed thereon and electrically connected to the bio-signal acquisition module, and at least one movable decorative model is disposed in the transparent container; wherein, according to the physiological indices of the user, the bio-signal acquisition module controls the actuator to switch on and switch off a rotational movement and to change a rotational speed, so that the at least one movable decorative model is moved correspondingly and provides a feedback of the physiological state of the user in real time.

In certain embodiments, the transparent device further includes a wireless data transmission module and a wireless data transmission antenna that are electrically connected to the bio-signal acquisition module for receiving and transmitting various physiological data of the user to an electronic device by using at least one of BLUETOOTH®, Wi-Fi, and infrared (IR) wireless data transmission technologies.

In certain embodiments, the electronic device is at least one of a mobile phone, a wearable device, a tablet computer, a laptop computer, and a desktop computer.

In certain embodiments, the physiological data of the user is accumulated to form a historical database that is stored in the electronic device and presented by a software application of the electronic device that serves as a platform for health management for the user and an interface for interacting with the user.

In certain embodiments, the transparent device further includes a power module that is electrically connected to the bio-signal acquisition module for providing power.

In certain embodiments, the power module is selected from at least one of a replaceable battery module, a rechargeable dry battery module, a detachable and rechargeable battery module, and a wireless rechargeable battery module.

These and other aspects of the present disclosure will become apparent from the following description of the embodiment taken in conjunction with the following drawings and their captions, although variations and modifications therein can be affected without departing from the spirit and scope of the novel concepts of the disclosure.

BRIEF DESCRIPTION OF THE DRAWINGS

The described embodiments can be better understood by reference to the following description and the accompanying drawings, in which.

DETAILED DESCRIPTION OF THE EXEMPLARY EMBODIMENTS

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 1:
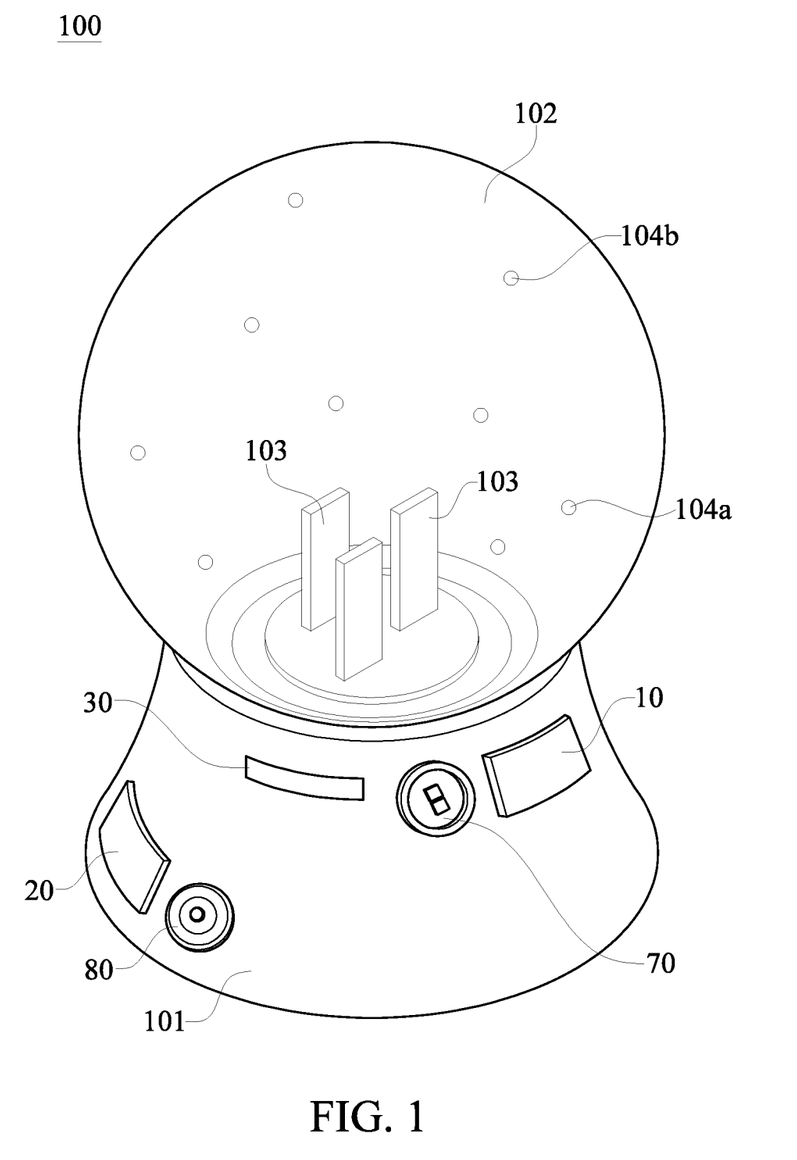
FIG. 1 is a perspective view of one embodiment of the present disclosure.
Figure 2:
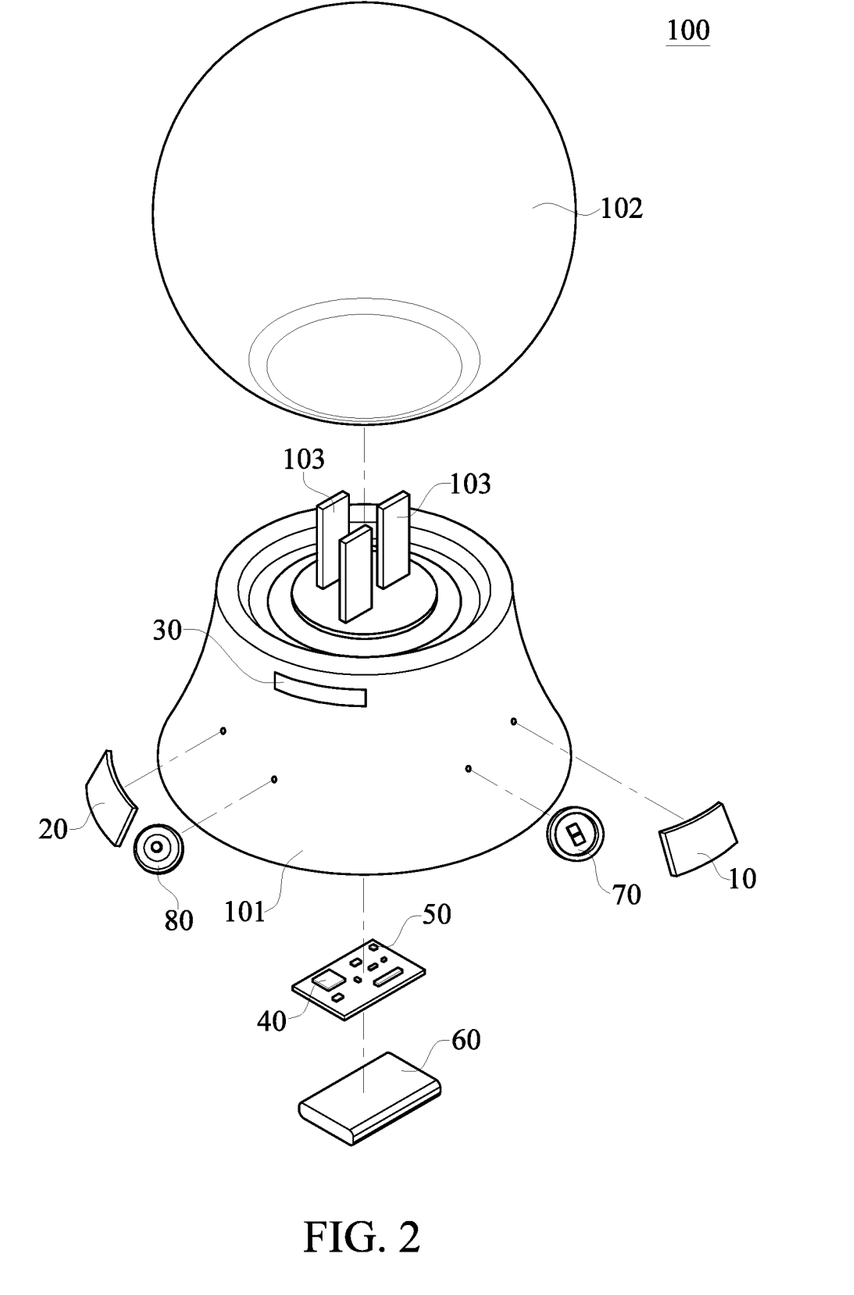
FIG. 2 is a perspective exploded view of one embodiment of the present disclosure.
Figure 3:
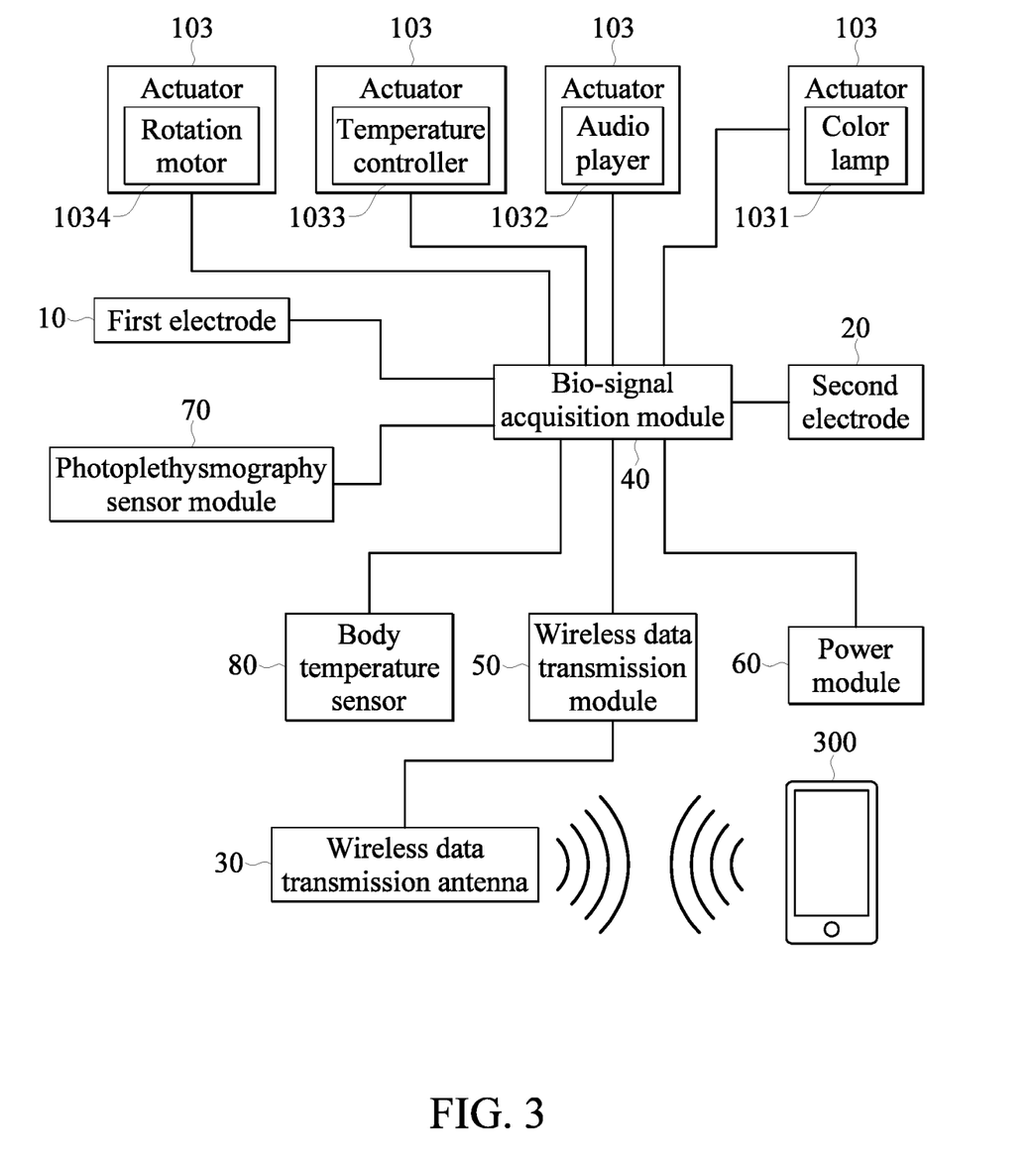
FIG. 3 is a block diagram of one embodiment of the present disclosure.

Referring to FIGS. 1 to 3, embodiments of the present disclosure provide a transparent device 100 with bio-signal acquisition and feedback capabilities.

The transparent device 100 (hereinafter referred to as the transparent device 100) of this embodiment includes a base 101, a transparent container 102, a first electrode 10, a second electrode 20, a wireless data transmission antenna 30, and a bio-signal acquisition module 40.

A shape of the base 101 of this embodiment can be appropriately varied according to practical requirements, and is not limited thereto. The bio-signal acquisition module 40 can be disposed at an appropriate location in the base 101, or can be a built-in assembly that is included as a part of the base 101. Further, in addition to the abovementioned modules, the transparent device 100 of this embodiment may include a wireless data transmission module 50 and a power module 60. The wireless data transmission antenna 30, the wireless data transmission module 50, and the power module 60 can be disposed at appropriate locations in the base 101, or can be built-in and included as a part of the base 101. Further, the transparent device 100 of this embodiment can include a photoplethysmography (PPG) sensor module 70 and a body temperature sensor 80.

The transparent container 102 of this embodiment can be a variety of light-transmitting materials, such as glass, plastic, ester, and the like, and one-piece molded or assembled into a container that has an appropriate shape, and can be filled up, and can also be in a variety of light-transmitting colors, or have light-transmitting color films or pigments on the surface of the container. The transparent container 102 can have a spherical, a polygonal, or an irregular shape, and is not limited thereto. Further, the transparent container 102 can also be assembled to and detachable from the base 101.

The first electrode 10 of this embodiment is disposed on a position on a side surface of the base 101 and is near a top surface of the base 101. The first electrode 10 is, for example, a positive electrode, and the first electrode 10 is made of an electrically conductive material, for example, at least one of a metal sheet, an electrically conductive silicone/film, a thin metal plating layer on the surface of the base 101, a thin metal coating layer, a thin metal sputter coating layer, and a thin metal sheet layer. Further, the material and shape of the first electrode 10 can be appropriately varied according to practical requirements or the shape of the base 101. The first electrode 10 can be electrically connected to the bio-signal acquisition module 40 through a conductive path, such as a metal wire, a thin film, or a plating layer.

The second electrode 20 of this embodiment is disposed on a position on the side surface of the base 101 and is near a bottom surface of the base 101, and the second electrode 20 is spaced from the first electrode 10. The second electrode 20 is, for example, a negative electrode, and the second electrode 20 is made of an electrically conductive material, for example, at least one of a metal sheet, an electrically conductive silicone/film, a thin metal plating layer on the surface of the base 101, a thin metal coating layer, a thin metal sputter coating layer, and a thin metal sheet layer. Further, the material and shape of the second electrode 20 can be appropriately varied according to practical requirements or the shape of the base 101. The second electrode 20 can be electrically connected to the bio-signal acquisition module 40 through a conductive path, such as a metal wire, a thin film, or a plating layer. In some embodiments, a grounding electrode can be provided.

The bio-signal acquisition module 40 of this embodiment can be disposed at the bottom of the base 101 and electrically connected to the first electrode 10 and the second electrode 20, and detect and acquire bio-signals from the user through the first electrode 10 and the second electrode 20. In one embodiment, the bio-signal acquisition module 40 includes an electrocardiographic (ECG) sensing circuit or an integrated circuit, and when both hands of the user are respectively in contact with the first electrode 10 and the second electrode 20, the body (e.g., the heart of the user) and the bio-signal acquisition module 40 form a closed-loop circuit so that the bio-signal acquisition module 40 can detect cardiac signals of the user and instantly record the current measurement to generate an electrocardiogram. In another embodiment, the bio-signal acquisition module 40 can receive electrical signals from the photoplethysmography (PPG) sensor module 70. When the hands of the user touches the PPG sensor module 70, the photoplethysmography (PPG) signals of the flowing substances in the blood can be detected during the pulses of the blood vessels, thereby calculating various physiological data (physiological index) such as the heart rate or various physiological data related to the blood. In detail, electrocardiogram (ECG or EKG) sensing is to sense cardiac signals of the user. That is, each time the heart beats and the myocardial cells are depolarized, a small electrical change can be detected on the surface of the limb skins through the standard limb lead (lead I) design. This small change can be captured and amplified by the ECG sensing circuit or the integrated circuit, and then the electrocardiogram can be drawn and recorded, a process of which is well known to persons skilled in the art and therefore will not be further described. Since the signals are weak and can be easily interfered with, the integrated circuits of the amplifying circuit and the filtering circuit can be integrated into the bio-signal acquisition module 40 to amplify the weak signals and reduce the noise of the signals, so as to ensure the accuracy of detection and recording.

The base 101 of this embodiment has at least one actuator 103, and the at least one actuator 103 extends into the transparent container 102. Further, the bio-signal acquisition module 40 is electrically connected to the at least one actuator 103, and the bio-signal acquisition module 40 controls the at least one actuator 103 to provide corresponding visual or auditory feedback in real time according to various physiological indices of the user. For example, one of the actuators 103 (i.e., a first actuator) has a color lamp 1031 disposed thereon and electrically connected to the bio-signal acquisition module 40, and another one of the actuators 103 (i.e., a second actuator) has an audio player 1032 disposed thereon and electrically connected to the bio-signal acquisition module 40, so that physiological state of the user, such as heart rate, is fed back in real time through the interactive sound and light effects of the music activation and volume change of the audio player 1032, and the color lamp 1031 being switched on and switched off, and a change of light color. Further, yet another one of the actuators 103 (i.e., a third actuator) has a temperature controller 1033 disposed thereon and electrically connected to the bio-signal acquisition module 40 to control a change of temperature through the temperature controller 1033, and at least one color-changeable decorative model 104a that senses changes in temperature can be disposed in the transparent container 102, so that the color-changeable decorative model 104a in the transparent container 102 produces a corresponding visual effect of change in color through temperature control generated by the temperature controller, thereby providing a feedback on the physiological state of the user in real time so that the user can intuitively understand his/her own physiological state. Further, the reference index such as caffeine intake index can be provided to the user.

It is worth mentioning that, in this embodiment, still another one of the actuators 103 (i.e., a fourth actuator) has a rotation motor 1034 disposed thereon and electrically connected to the bio-signal acquisition module 40. According to the physiological indices of the user, the bio-signal acquisition module 40 controls the actuator 103 to switch on and off a rotational movement and to change a rotational speed, so that a feedback on the physiological state of the user is provided in real time. Further, the transparent container 102 can have at least one decorative model 104b (e.g., a movable model) disposed therein, and can have liquids and small fragments filled therein. Therefore, physiological data of the user, such as a rapid heart rate, can prompt the actuator 103 to switch on, or to rotate from a low speed to a high speed, so that the decorative model 104b produces a visual change effect of performing actions or having the small fragments move at high speed within the transparent container 102. In this embodiment, a feedback of the physiological state of the user can be provided in real time.

In this embodiment, the transparent device 100 with bio-signal acquisition and feedback capabilities has a photoplethysmography (PPG) sensor module 70 that is expandable, such as a photoplethysmography (PPG) sensor, and the signal output from the photoplethysmography sensor module 70 is a photoplethysmography (PPG) signal.

In detail, the PPG sensor module 70 uses an optical penetration and reflection manner, and the principle of light sensing element absorbing light energy, so as to detect changes in the amount of light absorbed and reflected by substances flowing through the blood vessels and blood in peripheral blood vessels (such as small arteries) when heart pulsates. Further, since the blood flow in the blood vessels changes periodically according to heartbeat, the PPG sensor module 70 senses the flow or concentration changes of the blood vessel tissue or blood content by illuminating the blood vessels under the skins with lights of different wavelengths and using the intensity of reflected lights. At the same time, the period of the PPG signal also corresponds to the period of heartbeat. That is, the PPG signal is the electrical signal generated in response to the flow or concentration in the blood vessel tissue or blood detected by the PPG sensor module 70 by using a light sensing element, details of which are well known to persons skilled in the art and will not be further described herein. In the present embodiment, the PPG sensor module 70 may be exposed from or built-in in the base 101, and electrically connected to the bio-signal acquisition module 40. When fingers of the user touch the PPG sensor module 70, the bio-signal acquisition module 40 can calculate the physiological data of the user, such as peripheral oxygen saturation, as a reference for health management according to the physiological data obtained by the PPG sensor module 70. Moreover, with both the PPG signals and the ECG signals, more physiological data of the user can be estimated, such as relative blood pressure estimates.

In this embodiment, the transparent device 100 with bio-signal acquisition and feedback capabilities can have a body temperature sensor 80 that is expandable, which can be an electronic thermometer or an infrared thermometer electrically connected to the bio-signal acquisition module 40 for obtaining a temperature signal when contacting the hands of the user. When the fingers of the user touch the body temperature sensor 80, the bio-signal acquisition module 40 can calculate and record a body temperature of the user based on the electrical signal obtained from the body temperature sensor 80.

In this embodiment, the wireless data transmission module 50 can be disposed at the bottom of the base 101 and electrically connected between the wireless data transmission antenna 30 and the bio-signal acquisition module 40. The bio-signal acquisition module 40 can send original physiological detection data of the user to the wireless data transmission module 50, and the wireless data transmission module 50 transmits real-time physiological detection data of the user through the wireless data transmission antenna 30 in a wireless transmission manner, such as BLUETOOTH®, Wi-Fi, or infrared wireless data transmission technologies, to an electronic device 300, such as a mobile phone, a wearable device, a tablet computer, a laptop computer, and a desktop computer, and determines various application information, such as a body temperature, a heart rate, a heart rate variability, a heart age, a peripheral oxygen saturation, a blood pressure estimate, a risk alert for excessive heart rate, a mood index, a stress index, a caffeine intake index, a heart risk index and the like, by combining various algorithms on the bio-signal acquisition module 40 or the electronic device.

In addition, the wireless data transmission antenna 30 can be at least one of a thin metal plating layer, a thin metal coating layer, a thin metal sputter coating layer, and a thin metal sheet layer on the surface of the base 101.

The power module 60 of this embodiment can be disposed at the bottom of the base 101 and electrically connected to the bio-signal acquisition module 40 to provide a power of each module. The power module 60 can be a replaceable battery module, a rechargeable dry battery module, or a detachable and rechargeable battery module, or a wireless rechargeable battery module.

Figure 4:
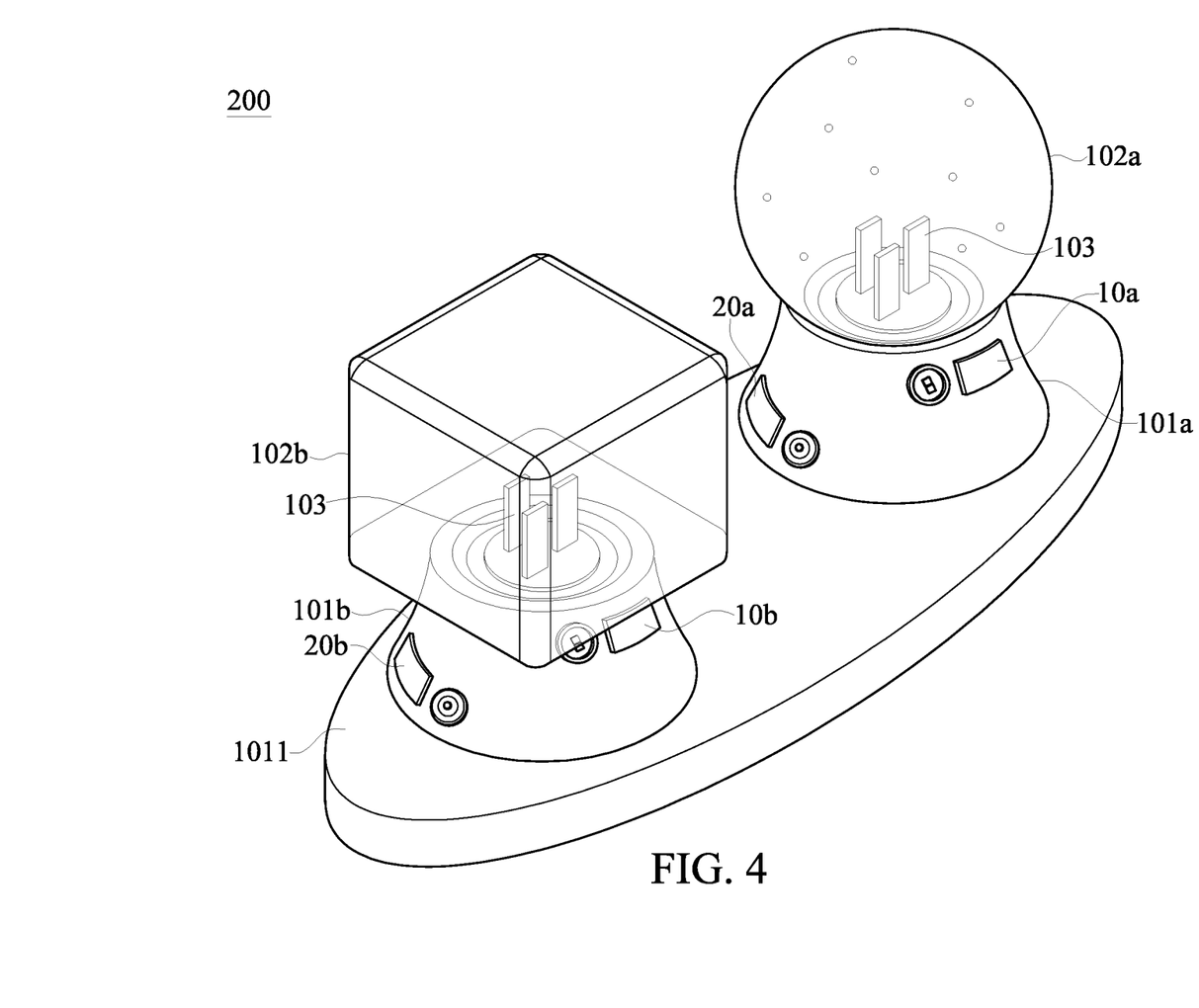
FIG. 4 is a perspective view of another embodiment of the present disclosure.

Referring to FIG. 4, this embodiment of the present disclosure further provides a transparent device 200 (hereinafter referred to as transparent device 200) with bio-signal acquisition and feedback capabilities.

In this embodiment, the transparent device 200 has a combination base 1011, two bases 101a, 101b, two transparent containers 102a, 102b, two first electrodes 10a, 10b, and two second electrodes 20a, 20b. The two bases 101a, 101b are disposed on the combination base 1011 and are spaced from each other, and the two transparent containers 102a, 102b, the two first electrodes 10a, 10b, and the two second electrodes 20a, 20b are respectively disposed on the two bases 101a, 101b, and the two bases 101a, 101b each has at least one actuator 103. The plurality of electrodes and the plurality of actuators of this embodiment are electrically connected to the bio-signal acquisition module. Therefore, the transparent device of this embodiment can be used by two users at the same time, so as to respectively generate different visual or auditory feedbacks for the two users, thereby further increasing the fun and interactivity between the two users.

It should be noted that, in this embodiment, two transparent containers are provided, but a quantity of the transparent containers is not limited thereto in the present disclosure, and can be more than two in other embodiments. Further, the two transparent containers of this embodiment are not of a same appearance, one of which is spherical, and the other of which is polygonal, but can also be irregular shaped in other embodiments of the present disclosure.

Furthermore, the abovementioned descriptions describe differences between this embodiment and other embodiments, and similarities therebetween are not repeated herein.

In summary, the present disclosure provides a transparent device with bio-signal acquisition and feedback capabilities, which includes a first electrode, a second electrode, a photoplethysmography sensor module, a body temperature sensor, and a bio-signal acquisition module that are disposed at the base of the device, and the base of the device has at least one actuator that extends into the transparent container, so that the bio-signal acquisition module controls, according to physiological indices of a user, at least one actuator to provide corresponding visual or auditory feedback in real time. Therefore, the user can measure bio-signals just by holding the base of the device, and measurement of the bio-signal can be completed without any additional burden in connection with wearable devices or forced habits, and the corresponding visual or auditory feedback can be obtained in real time through the transparent container.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A transparent device with bio-signal acquisition and feedback capabilities, comprising:
    a base including at least one actuator;
    a transparent container connected to the base, wherein the at least one actuator extends into the transparent container;
    a first electrode disposed on the base;
    a second electrode disposed on the base;
    a body temperature sensor disposed on the base;
    a photoplethysmography (PPG) sensor module disposed on the base; and
    a bio-signal acquisition module having an electrocardiogramar (ECG or EKG) sensor function,
    wherein the bio-signal acquisition module is electrically connected to the first electrode and the second electrode for acquiring an ECG signal,
    wherein the bio-signal acquisition module is electrically connected to the PPG sensor module for acquiring a PPG signal,
    wherein the bio-signal acquisition module is electrically connected to the body temperature sensor for acquiring a body temperature signal,
    wherein the bio-signal acquisition module is electrically connected to the at least one actuator,
    wherein the at least one actuator has a rotation motor disposed thereon and electrically connected to the bio-signal acquisition module and at least one movable fragment is disposed in the transparent container,
    wherein the bio-signal acquisition module is configured to control the at least one actuator based on the ECG signal, the PPG signal and the body temperature signal to switch on and switch off a rotational movement of the at least one actuator and to change a rotational speed of the at least one actuator, so that the at least one movable fragment is moved correspondingly and provides a feedback of a physiological state of a user in real time.

2. The transparent device according to claim 1, wherein the at least one actuator has a color lamp that is electrically connected to the bio-signal acquisition module, so as to provide the feedback of the physiological state of the user in real time through the color lamp being switched on and switched off, and a change of light color.

3. The transparent device according to claim 1, wherein the at least one actuator has an audio player that is electrically connected to the bio-signal acquisition module, so as to provide the feedback of the physiological state of the user in real time through an activation of music and a change of volume of the audio player.

4. The transparent device according to claim 1, further comprising a wireless data transmission module and a wireless data transmission antenna that are electrically connected to the bio-signal acquisition module for receiving and transmitting various physiological data of the user to an electronic device by using at least one of BLUETOOTH®, Wi-Fi, and infrared (IR) wireless data transmission technologies.

5. The transparent device according to claim 4, wherein the electronic device is at least one of a mobile phone, a wearable device, a tablet computer, a laptop computer, and a desktop computer.

6. The transparent device according to claim 1, further comprising a power module that is electrically connected to the bio-signal acquisition module for providing power.

7. The transparent device according to claim 6, wherein the power module is selected from at least one of a replaceable battery module, a rechargeable dry battery module, a detachable and rechargeable battery module, and a wireless rechargeable battery module.

* * * * *